(12) United States Patent
Kilpatrick-Liverman et al.

(10) Patent No.: US 6,265,364 B1
(45) Date of Patent: Jul. 24, 2001

(54) SOLID CLEANSING COMPOSITION COMPRISING A CHOLINE SALT

(75) Inventors: LaTonya Kilpatrick-Liverman, Princeton; Zeenat Nabi, Cranbury; Thomas G. Polefka, Somerset, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/473,590

(22) Filed: Dec. 28, 1999

(51) Int. Cl.$^7$ .................................................. C11D 1/62
(52) U.S. Cl. .................. 510/133; 510/119; 510/120; 510/130; 510/132; 510/135; 510/136; 510/141; 510/158; 510/159; 510/499; 510/504
(58) Field of Search ..................................... 510/119, 120, 510/130, 132, 133, 135, 136, 141, 158, 159, 499, 304

(56) References Cited

U.S. PATENT DOCUMENTS

| | | | |
|---|---|---|---|
| 4,839,159 | * 6/1989 | Winter et al. | 424/59 |
| 5,116,605 | * 5/1992 | Alt | 424/70 |
| 5,637,305 | * 6/1997 | Cavazza et al. | 424/401 |
| 5,804,205 | 9/1998 | Epstein et al. | 424/401 |
| 5,895,658 | * 4/1999 | Fossel | 424/401 |
| 5,922,331 | * 7/1999 | Mausner | 424/401 |
| 6,048,886 | * 4/2000 | Neigut | 514/412 |

FOREIGN PATENT DOCUMENTS

| | | | |
|---|---|---|---|
| WO96/27363 | 9/1996 | (EP) | A61K/7/06 |
| 96/27363 | * 9/1996 | (WO) | |
| 97/42942 | * 11/1997 | (WO) | |

OTHER PUBLICATIONS

Nau–Wagner et al., High Affinity Transport of Choline-O-Sulfate and It's Use as a Compatible Solute in *Bacillus subtilis*, Applied and Environmental Microbiology, Feb. 1999, pp. 560–568.

Ahlstrom et al., Lone Chain Alkanoylcholines, A New Category of Soft Antimicrobial Agents That Are Enzymatically Degradable, Antimicrobial Agents and Chemotherapy, Jan. 1995, pp. 50–55.

* cited by examiner

Primary Examiner—Mark Kopec
Assistant Examiner—Charles Boyer
(74) Attorney, Agent, or Firm—Martin B. Barancik

(57) ABSTRACT

A composition useful for moisturizing skin which comprises (a) a moisturizing effective amount of a compound of the structure:

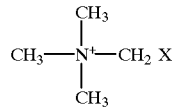

wherein X is selected from the group consisting of:

$CH_2OH$, CH OH $CH_2CO_2$—, or mixtures thereof wherein when X does not bear a negative charge, the said compound is a salt; and (b) a skin compatible carrier.

7 Claims, No Drawings

SOLID CLEANSING COMPOSITION COMPRISING A CHOLINE SALT

BACKGROUND OF THE INVENTION

Skin moisturization has been a desired skin benefit for many years. Dry skin can be a result of environmental effects such as sunlight, dry winter air, dermatological condition as well as the application of cleansing materials to the skin such as soap or other harsh detergents which remove oils that are naturally present on the surface of the skin thereby resulting in a loss of moisturization.

Often times the active ingredients used for the improvement of hair structure and skin surface are usually cationic surfactants in combination with various wax-type additives such as, for example, vaseline, fatty acid esters and fatty alcohols. According to WO 96/27363, however, hair and skin treatment agents on that basis, though, have satisfactory results only in the treatment of dry and porous hair, or dry and porous skin. This document then states that for the treatment of hair/skin that quickly replenishes the fat, they are not as well suited because when they are used, the natural fat replenishment is even increased. The document states the reasons for the strong replenishment of fat are especially the cationic emulsifiers contained in these agents. The document states that it was its task to make available a hair and/or skin treatment agent on the basis of conditioning active ingredient which does not have the disadvantages mentioned. Thereafter, the application discloses a cosmetic agent containing water and a combination of:

a. 0.1 to 25% by weight, of at least one choline salt of an inorganic acid or an organic carboxylic acid or a polyacrylic acid homo- or copolymer, and b. 0.1 to 10% by weight, of at least one physiologically compatible aliphatic organic acid.

It is then stated that the agent in accordance with the invention improves the ability of the hair to be combed wet, shows good compatibility with the scalp, and gives the hair a soft feel and a beautiful shine. It is further stated that the agent in accordance with the invention shows good compatibility with the skin and the eyes, gives the skin a well-groomed appearance, and is also biodegradable.

There is no information provided in the document as to the specific action of the choline salt on skin other than it "gives the skin a well groomed appearance". Example 5 of the document, a shampoo for hair and skin, states that the skin shows a smooth, soft skin surface after use. Example 6, a skin care cream, states that the skin feels smoother and supple after use. Example 7, an oil in water body lotion, states that the composition increases skin moisture and leaves a pleasant feeling. Present in Example 7 with 7 wt % of choline salts are also 10 wt % cetylstearyloctanoate, 5 wt % glycerine, 4 wt % cetylstearylalcohol, 3 wt % sorbitan stearate, and 1 wt % dimethyl polysiloxane. These latter materials are all well known moisturizing agents.

Nowhere in WO 96/27363 is there a clear definition of what "conditioning" agent means. Conditioning in general means making skin feel soft and smooth. A conditioning agent does not necessarily bring about moisturization. Such an agent is generally known as a moisturizing agent. Sometimes these two activities are broadly grouped under the category of "conditioning and moisturizing" agent.

We have now discovered that choline salt and related compounds are powerful moisturizing agents for skin. Even in a rinse off cleansing composition such material(s) or mixture thereof brings about substantially more moisture on the skin. This can be a statistically significant measurable quantity of moisture on the skin.

SUMMARY OF THE INVENTION

In accordance with the invention, there is a cosmetic composition comprising a. a moisturizing effective amount of a compound of the formula

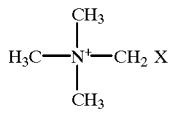

wherein X is selected from the group consisting of:

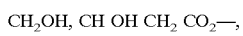

or mixtures thereof with the proviso that when X does not bear a negative charge, the compound is a salt and (b) a skin compatible carrier for the said compound. Such counterion making the salt is derived from an inorganic acid such as hydrochloric, sulfuric, phosphoric and the like or organic acids such as acetic, lactic, citric and the like.

The composition can be used to moisturize the skin. Significant measurable increases in moisture can be obtained when the composition is applied to the skin. The composition can be in the form of a liquid, solid, or gelled cleansing formulation. Such liquids or gels can be in various cosmetic forms such as lotion, cream and the like. A desirable form is a liquid cleansing composition. The preferred compound is a salt of choline, for example, the chloride salt. When using a salt of choline, a physiologically compatible aliphatic organic acid need not be present in the composition in the range of about 0.05 to about 15 percent by weight of the composition, or even about 0.1 to about 10 wt % of the composition. In fact, such physiologically compatible aliphatic organic acid need not be present in the composition at all. If a physiologically compatible aliphatic organic acid is present in the composition, it is desirably less than about 0.05 wt % or above about 15 wt % of the composition.

DETAILED DESCRIPTION OF THE EMBODIMENT

The moisturizing compound can be formulated into a variety of compositions, liquid, solid and gel-like for delivery of its moisturizing benefit. When formulated with a solid, the moisturizing compound can be present with large or small quantities of soap with the remainder of the surfactant being none, smaller or larger quantities of anionic surfactant such as synthetic surfactant. When formulated with a liquid or gel composition, the moisturizing compound is formulated with various amounts of water depending upon the usage of the composition as a cleansing composition, as well as various surfactants of an anionic, nonionic, cationic, amphoteric type, or mixtures thereof. The liquid or gel formulations, particularly the liquids can be formed as a cream or lotion or free flowing liquid which has cleaning abilities, moisturizing and/or conditioning abilities, or a mixture of the cleansing with the moisturizing and/or conditioning benefits. By conditioning is meant increasing the smoothness or suppleness of the skin. By moisturizing is meant the actual increasing of water content of the skin.

Other conditioning and moisturizing agents also can be present in the compositions of the invention. Typical moisturizing or conditioning materials include urea, lactic acid, pyrrolidone carboxylic acid, amino acids and salts of the acids mentioned.

Occlusive agents are further examples of substances which can be present in the composition. These are substances which form on the skin thin films of limited permeability, serving to hold water within the skin and prevent dehydration. The range of occlusive agents is considerable. They are generally hydrophobic oils and waxes. Examples of classes of such agents and individual examples of such agents are:
1. Hydrocarbon oils and waxes. Examples thereof are mineral oil, petrolatum, paraffin, ceresin, ozokenite, microcrystalline wax.
2. Silicone oils, such as dimethyl polysiloxanes, methylphenyl polysiloxanes, silicone glycol copolymers.
3. Triglyceride esters, for example, vegetable and animal fats and oils.
4. Glyceride esters and esters such as acetylated monoglycerides, and ethoxylated monoglycerides.
5. Alkyl and alkenyl esters of fatty acids having 10 to 20 carbon atoms. Examples include hexyl laurate, isohexyl laurate, isohexyl palmitate, isopropyl myristate, isopropyl palmitate, decyl oleate, isodecyl oleate, hexadecyl stearate, decyl stearate, isopropyl isostearate, diisopropyl adipate, diisohexyl adipate, dihexyl decyl adipate, diisopropyl sebacate, lauryl lactate, myristyl lactate, cetyl lactate, oleyl myristate, oleyl stearate and oleyl oleate.
6. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanyl alcohols are examples of satisfactory fatty alcohols.
7. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols and lanolin alcohols (inoleate are illustrative emollients derived from lanolin.
8. Natural waxes, esters thereof and ethoxylated natural waxes, beeswax, spermaceti, myristyl myristate, stearyl stearate, polyoxyethylene sorbitol beeswax, carnauba wax and candelilla wax.

Especially desirable are $C_2$–$C_4$ alkyl esters of $C_{12}$–$C_{18}$ fatty acids, such as isopropyl myristate, and isopropyl palmitate and petrolatum.

Humectants can also be present in the composition and are especially $C_2$–$C_6$ polyols notably glycerol, sorbitol, propylene glycol and 1,3-butylene glycol. A further example of humectant is polyethylene glycols having molecular weights of from about 100 to about 1500. Humectants do not themselves form occlusive films but may cooperate with other materials to form a film having occlusive properties. It is, therefore, desirable that humectants are not the sole category of skin emollient agent present.

Examples of surfactant which can be employed in the composition include anionic, nonionic, amphoteric and cationic.

Any anionic surfactant can be employed. Examples of such anionic surfactants include soap, a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art for example taurates, phosphate, and those listed in the *Mr. Cutcheon's Encyclopedia of Surfactants*.

Although not necessary other surfactants may be present in the composition. Examples of these surfactants include zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

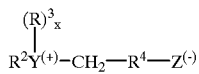

wherein $R^2$ contains an alkyl, alkenyl, or hydroxy alkyl radical of from about 8 to about 18 carbon atoms, from 0 to about 10 ethylene oxide moieties and from 0 to 10 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include:
   4-[N,N-di(2-hydroxyethyl)-N-octadecylammonio]-butane-1-carboxylate;
   5-[S-3-hydroxypropyl-S-hexadecylsulfonio]-3 hydroxy-pentane-1-sulfate
   3-[P,P,P-diethyl-P 3,6,9 trioxatetradecyl-phosphonio]-2-hydroxypropane-1-phosphate
   3-[N,N-dipropyl-N-3 dodecoxy-2-hydroxy-propylammonio]-propane-1-phosphonate
   3-(N,N-di- methyl-N-hexadecyl-ammonio) propane-1-sulfonate; 3-(N,N-dimethyl-N-hexadecylammonio)-2-hydroxypropane-1-sulfonate
   4-(N,N-di(2-hydroxyethyl)-N-(2 hydroxydodecyl) ammonio]-butane-1-carboxylate
   3-[S-ethyl-S-(3-dodecoxy-2-hydroxy-propyl) sulfonio]-propane-1-phosphate 3-(P,P-dimethyl-P-dodecylphosphonio)-propane-1-phosphonate; and 5-[N,N-di(3-hydroxypropyl)-N-hexadecyl-ammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:
 stearyldimethylbenzyl ammonium chloride;
 dodecyltrimethylammonium chloride;
 nonylbenzylethyldimethyl ammonium nitrate;
 tetradecylpyridinium bromide;
 laurylpyridinium chloride;
 cetylpyridinium chloride
 laurylpyridinium chloride;
 laurylisoquinolium bromide;
 ditallow(hydrogenated)dimethyl ammonium chloride;
 dilauryldimethyl ammonium chloride; and
 stearalkonium chloride.

Additional cationic surfactants are disclosed in U.S. Pat. No. 4,303,543. See column 4, lines 58 and column 5, lines 1–42, incorporated herein by references. Also see *CTFA Cosmetic Ingredient Dictionary, 4th Edition* 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$R_1R_2R_3N \rightarrow O$ wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyl-dimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$RR'R''P \rightarrow O$ wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond.

Examples of suitable phosphine oxides are:
 dodecyldimethylphosphine oxide,
  tetradecylmethylethyl-phosphine oxide,
 3,6,9-trioxaoctadecyldimethyl-phosphine oxide,
  cetyldimethylphosphine oxide,
 3-dodecoxy-2-hydroxypropyldi(2-hydroxyethyl) phosphine oxide stearyldimethyl-phosphine oxide,
 cetylethyl propylphosphine oxide, oleyldiethylphosphine oxide,
 dodecyldiethylphosphine oxide, tetradecyldiethylphosphine oxide,
 dodecyldipropylphosphine oxide, dodecyldi(hydroxymethyl)phosphine oxide, dodecyldi(2-hydroxy-ethyl)phosphine oxide, tetradecyl-methyl-2-droxypropylphosphine oxide, oleyldimethylphosphine oxide, and 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides include wherein the alkyl group is from about 8 to 20 carbon atoms, preferably about 10 to about 18 carbon atoms and the degree of polymerization of the glycoside is from about 1 to about 3, preferably about 1.3 to about 2.0.

The quantities of the moisturizing compound or mixtures thereof of the invention which can be employed is any moisturizing effective amount. Generally there is at least about 0.1 wt % of the composition, desirably at least about 0.5 wt % of the composition, and more desirably at least about 1 wt % of the composition as the compound or mixtures thereof of the invention. Generally, no more than about 20 wt % of the composition is the moisturizing agent or mixtures thereof of the invention, desirably no more than about 10 to 15 wt % of the composition. The desirability of the quantity is generally the balance between the desirable qualities of the compound or mixtures versus any undesirable effects such material(s) might have on the overall composition effects.

Surfactants can be present in a composition wherein cleansing is not a goal but emulsification of any conditioning agent in the composition is desirable. Generally a minimum of about 0.5 wt % of surfactants can be employed for emulsification purposes. Therefore, an emulsifying quantity of surfactant can be employed. Surfactants can also be employed in a composition wherein cleansing is a goal. A cleansing effective amount should be employed. For cleaning purposes, at least about 1 wt %, desirably at least about 2 or 3 wt % of surfactant is desirable.

Following are examples of the invention. These examples are intended to illustrate the invention rather than limit the invention. Similar results are expected with all the compounds of the invention other than choline salt per se. As the results clearly show, a choline salt brings about moisturization of skin. These results are at least somewhat related to the fact that choline salt is substantive to the skin in a rinse off formulation. Typical humectants such as ethylene glycol and glycerine show no substantivity to skin in rinse off formulations.

EXAMPLE 1

The epidermis of full thickness pig skin (Animal Technologies, Tyler, Tex.) was removed using a Packard Instruments dermatome, and the stratum corneum was removed via trypsin digestion. Pieces of stratum corneum were then immersed in millipore water, a 5% choline chloride (Aldrich Chemical, Milwaukee, Wis.), or a 5% glycerin solution. Using a dynamic vapour sorption meter (Surface Measurement Systems, Coopersburg, Pa.), the skin was equilibrated under a 0% relative humidity environment until the change in weight varied no more than 0.005% per min. This weight was recorded as the dry weight. The relative humidity was then increased to 90%. The skin was equilibrated at this humidity until the change in weight varied no more than 0.005% per min. This weight was, likewise, recorded and the % water uptake was calculated. The table below shows the humectancy power of choline. Based on our results, it is comparable to that of glycerin.

| Sample | % Water Uptake |
| --- | --- |
| Water | 27 ± 1 |
| 5% Choline | 89 ± 14 |
| 5% Glycerin | 75 ± 6 |

EXAMPLE 2

3 cm×8 cm pig skin (Animal Technologies, Tyler, Tex.) was washed with 1 ml of a shower gel (control) or 1 ml of a shower gel containing 5% choline chloride salt. The skin was washed for 2 minutes followed by a 15 second rinse. The stratum corneum was then removed via trypsin digestion. Using a dynamic vapour sorption meter (Surface Measurement Systems, Coopersburg, Pa.), the skin was equilibrated under a 0% relative humidity environment until the change in weight varied no more than 0.005% per min. This weight was recorded as the dry weight. The relative humidity was then increased to 90%. The skin was equilibrated at this humidity until the change in weight varied no more than 0.005% per min. This weight was, likewise, recorded and the % water uptake was calculated. The table below shows the results (% water uptake) of pig skin treated with shower gel and shower gel plus 5% choline.

| Sample | % Water Uptake |
| --- | --- |
| Shower Gel | 25 ± 1 |
| Shower Gel + 5% Choline | 34 ± 4 |

EXAMPLE 3

The radiolabelling experiment described in this example was carried out to quantify the amount of choline that could adhere to the skin following a water rinse. Full thickness Yucatan swine skin (Charles River, Inc., Wilmington, Mass.) was mounted (dermis side down) onto a special sample holder, the dimensions of which were previously described in U.S. Pat. No. 4,836,014. This sample holder exposed approximately 4.91 cm$^2$ of the skin. A 1 ml aliquot of ($^3$H$_3$C)-choline (American Radiolabel Chemicals, Inc., St. Louis, Mo.) containing shower gel was next applied to the surface of the exposed skin. This shower gel was prepared by adding 100 mg of choline chloride (Aldrich Chemical, Milwaukee, Wis.) and 2 $\mu$Ci of $^3$H-choline to 20 ml of a 25% shower gel solution (i.e., 25 grams of shower gel diluted into 75 grams of distilled water). After five minutes had elapsed, the shower gel was removed, and the surface of the skin was rinsed with 10 ml of distilled water. A second 1 ml aliquot of the ($^3H_3C$)-choline containing shower gel was then reapplied to the skin. Again, after a 5 minute exposure time, the shower gel was removed and the skin rinsed with 10 ml of distilled water. The skin sample was then removed from its sample holder and air-dried for 10 minutes. Four 4 mm diameter punches were collected from each piece of treated skin, oxidized in a Packard oxidizer, and counted in a Packard 2000 Tri-carb liquid scintillation analyzer (Packard Instruments Inc., Downers Grove, Ill.). To obtain the specific activity, 0.1 ml of the ($^3H3C$)-choline containing shower gel was counted in the Packard 2000 analyzer. Based on the results, the amount of choline remaining on the skin following a water rinse was 33 $\mu g/cm^2$.

EXAMPLE 4

A shower gel composition containing choline chloride useful in the method of this invention is prepared as below, starting with water and adding each component thereafter in the order given, each addition accompanied by stirring to obtain compatibility.

| Shower Gel Composition | |
|---|---|
| Ingredient | % |
| Water | 43.96 |
| Glycerin (99.5%) | 0.40 |
| Ammonium Lauryl Sulfate (28%) | 40.00 |
| Cocoamidopropyl Betaine (30%) | 5.00 |
| Polyquaternium-7 (8%) | 1.50 |
| Tetrasodium EDTA (39%) | 0.13 |
| Coconut Diethanolamide (100%) | 1.00 |
| Choline Chloride | 5.00 |
| Fragrance | 0.65 |
| 1,2-Dibromo-2,4-dicyanobutane-10% in Dipropylene Glycol | 0.30 |
| Glycol Distearate & Laureth-4 & Cocamidopropyl Betaine (45%) | 2.00 |
| Citric acid-anhydrous | 0.06 |

Following are examples of a lotion and a cream composition, each containing a choline salt which will provide skin moisturization.

| Ingredient | % |
|---|---|
| LOTION | |
| Water | 81.41 |
| Choline Chloride | 2.00 |
| Magnesium Aluminum Silicate | 0.08 |
| Glycerin | 2.60 |
| Glyceryl/PEG-100 Stearate | 1.60 |
| Sodium Cetearyl Sulphate | 0.32 |
| Cetearyl Alcohol | 0.60 |
| Mineral Oil-Light | 4.00 |
| Dimethicone | 0.80 |
| Petrolatum | 1.00 |
| Tocopheryl Acetate | 0.50 |
| Isopropyl Palmitate | 2.60 |
| Carbomer 2984 | 0.30 |
| Deionized Water | 1.00 |
| 99% Triethanolamine | 0.30 |
| Phenoxyethanol | 0.15 |

| -continued | |
|---|---|
| Ingredient | % |
| Methyldibromo Glutaronitrile | 0.10 |
| Fragrance | 0.30 |
| Polysorbate 60 | 0.16 |
| Vitamin A Palmitate | 0.08 |
| D Panthenol 50-P | 0.10 |
| TOTAL | 100.00 |
| CREAM | |
| Water | 77.60 |
| Choline Acetate | 4.00 |
| Magnesium Aluminum Silicate | 0.10 |
| Glycerin | 2.00 |
| Glyceryl Stearate/PEG-100 Stearate | 2.00 |
| Sodium Cetearyl Sulphate | 0.32 |
| Isohexadecane | 1.50 |
| Cetyl-Stearyl Alcohol 50-50 | 0.75 |
| Mineral Oil-Light | 5.00 |
| Dimethicone | 1.00 |
| Petrolatum | 1.25 |
| Tocopheryl Acetate | 0.50 |
| Isopropyl Palmitate | 2.00 |
| Carbomer 2984 | 0.36 |
| 99% Triethanolamine | 0.36 |
| Fragrance | 0.30 |
| Phenoxyethanol | 0.15 |
| Methyldibromo Glutaronitrile | 0.10 |
| Polysorbate 60 | 0.20 |
| Vitamin A Palmitate | 0.01 |
| D Panthenol 50-P | 0.50 |
| TOTAL | 100.00 |

What is claimed is:

1. A solid cleansing composition suitable for moisturizing skin which comprises, (a) a moisturizing effective amount of a choline salt or mixture thereof wherein choline is of the formula

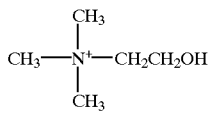

and the counterion is derived from an inorganic acid or an organic acid, (b) a skin compatible carrier, and (c) at least about 3 wt. % soap.

2. The composition in accordance with claim 1 wherein there is less than about 0.05 wt % or above about 15 wt % of a physiologically compatible aliphatic organic acid present in the composition.

3. The composition in accordance with claim 1 wherein a cleansing effective amount of a surfactant or mixture of surfactants is in the composition.

4. The composition in accordance with claim 1 wherein the composition has a skin conditioning effective amount of an emollient.

5. The composition in accordance with claim 4 wherein the emollient is selected from the group consisting of a moisturizing agent, an occlusive agent and a humectant.

6. A process for increasing the moisture level of skin which comprises applying the composition of claim 1 to the skin.

7. The process in accordance with claim 6 wherein there is less than about 0.05 wt % or above about 15 wt % of a physiologically compatible aliphatic organic acid present in the composition.

* * * * *